United States Patent
Cho et al.

(10) Patent No.: US 10,413,204 B2
(45) Date of Patent: Sep. 17, 2019

(54) APPARATUS AND METHOD FOR BRAIN COMPUTER INTERFACE

(71) Applicant: GWANGJU INSTITUTE OF SCIENCE AND TECHNOLOGY, Gwangju (KR)

(72) Inventors: Hohyun Cho, Gwangju (KR); Sung Chan Jun, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 323 days.

(21) Appl. No.: 15/362,818

(22) Filed: Nov. 29, 2016

(65) Prior Publication Data

US 2017/0238831 A1    Aug. 24, 2017

(30) Foreign Application Priority Data

Feb. 19, 2016    (KR) .................. 10-2016-0019607

(51) Int. Cl.
| | |
|---|---|
| A61B 5/04 | (2006.01) |
| A61B 5/0482 | (2006.01) |
| A61B 5/00 | (2006.01) |
| A61B 5/0476 | (2006.01) |
| G06F 3/01 | (2006.01) |
| G06K 9/00 | (2006.01) |

(52) U.S. Cl.
CPC ........ *A61B 5/04017* (2013.01); *A61B 5/0476* (2013.01); *A61B 5/7267* (2013.01); *G06F 3/015* (2013.01); *A61B 2560/0223* (2013.01); *G06K 9/00536* (2013.01)

(58) Field of Classification Search
None
See application file for complete search history.

(56) References Cited

PUBLICATIONS

Herbert Ramoser et al., "Optimal Spatial Filtering of Single Trial EEG During Imagined Hand Movement", IEEE Transactions on Rehabilitation Engineering, vol. 8, No. 4, Dec. 2000, pp. 441-446.
Benjamin Blankertz et al., "Optimizing Spatial Filters for Robust EEG Single-Trial Analysis" IEEE Signal Processing Magazine, vol. 25, Jan. 2008, pp. 41-56.
[Supportive Materials for Exception to Loss of Novelty] Hohyun Cho et al, "Increasing session-to-session transfer in a brain-computer interface with on-site background noise acquisition", Journal of Neural Engineering, 12, (2015), IOP Publishing, Published on Oct. 9, 2015, 16 pages.

*Primary Examiner* — Etsub D Berhanu
(74) *Attorney, Agent, or Firm* — Hauptman Ham, LLP

(57) ABSTRACT

The present disclosure discloses an apparatus for a brain computer interface (BCI) including a feature extraction filter trainer for training a feature extraction filter which minimizes an influence of a background brain wave while maximizing a difference between intended brain waves; and a classifier trainer for training a classifier for classifying the intended brain waves by using a feature vector obtained by filtering the intended brain wave at the feature extraction filter. With the apparatus, only the background brain wave is additionally measured, such that previous intended brain wave data can be reused and the brain wave can be classified more quickly and accurately.

8 Claims, 5 Drawing Sheets

FIG. 5

| Training session | Testing session | CSP (baseline) | iCSP with offline | iCSP with on-site | sCSP | RSTF with offline | RSTF with on-site | RSTF with on-site and RC |
|---|---|---|---|---|---|---|---|---|
| s1-1 | s1-2 | 80.0% | 60.0% | 91.4% | 60.0% | 80.7% | 89.3% | 91.4% |
| | s1-3 | 61.3% | 59.3% | 81.3% | 52.7% | 70.7% | 82.7% | 89.3% |
| | s1-4 | 78.7% | 74.7% | 88.7% | 80.7% | 50.0% | 93.3% | 92.7% |
| s2-1 | s2-2 | 50.0% | 50.0% | 79.3% | 72.7% | 50.0% | 86.7% | 85.3% |
| | s2-3 | 50.0% | 50.0% | 82.7% | 53.3% | 50.0% | 80.7% | 84.0% |
| s2-4 | s2-5 | 50.0% | 50.0% | 65.3% | 70.0% | 54.0% | 70.0% | 76.7% |
| s3-1 | s3-2 | 64.7% | 76.0% | 70.7% | 75.3% | 56.7% | 67.3% | 68.0% |
| | s3-3 | 50.7% | 54.7% | 50.0% | 48.7% | 57.3% | 49.3% | 43.3% |
| s3-4 | s3-5 | 67.3% | 56.7% | 60.0% | 68.0% | 66.7% | 64.7% | 68.0% |
| | s4-2 | 95.3% | 84.7% | 92.7% | 87.3% | 82.0% | 80.0% | 80.7% |
| s4-1 | s4-3 | 92.7% | 92.7% | 79.3% | 91.3% | 83.3% | 90.7% | 92.7% |
| | s4-4 | 65.3% | 90.0% | 93.3% | 87.3% | 51.3% | 88.7% | 89.3% |
| s5-1 | s5-2 | 51.3% | 50.7% | 87.3% | 62.7% | 52.0% | 92.7% | 88.7% |
| s6-1 | s6-2 | 81.0% | 84.0% | 84.0% | 79.0% | 87.0% | 88.0% | 89.0% |
| s7-1 | s7-2 | 62.0% | 59.0% | 54.0% | 62.0% | 62.0% | 63.0% | 60.0% |
| s8-1 | s8-2 | 60.0% | 61.3% | 59.3% | 64.0% | 60.0% | 63.3% | 63.3% |
| s9-1 | s9-2 | 52.0% | 66.7% | 50.0% | 56.7% | 60.7% | 66.0% | 66.7% |
| s10-1 | s10-2 | 96.0% | 96.0% | 92.7% | 97.3% | 95.3% | 96.7% | 98.7% |
| s11-1 | s11-2 | 78.7% | 80.7% | 79.3% | 82.7% | 79.3% | 80.0% | 80.0% |
| s12-1 | s12-2 | 66.7% | 72.7% | 70.7% | 77.3% | 80.0% | 81.3% | 82.7% |
| | Mean | 67.7% | 68.5% | 75.6% | 71.5% | 65.0% | 78.7% | 79.5% |
| | Median | 65.0% | 64.0% | 79.3% | 71.3% | 60.3% | 81.0% | 83.3% |
| | Standard deviation | 15.6% | 15.5% | 14.7% | 13.9% | 14.6% | 12.9% | 13.9% |

APPARATUS AND METHOD FOR BRAIN COMPUTER INTERFACE

CROSS REFERENCE TO RELATED APPLICATION

This application claims the benefit of Korean Patent Application No. 10-2016-0019607, filed on Feb. 19, 2016, entitled "APPARATUS AND METHOD FOR BRAIN COMPUTER INTERFACE", which is hereby incorporated by reference in its entirety into this application.

BACKGROUND

1. Technical Field

The present disclosure relates to an apparatus and method for a brain computer interface, and in particularly, to a technology for more quickly and accurately analyzing what a brain wave intends by measuring the brain wave.

2. Description of the Related Art

A brain computer interface (BCI) refers to means for connecting the brain of a creature with a computer to enable communications therebetween. The BCI directly connects the brain with the computer without conventional input/output devices using the creature's verbal or visual expressions. For example, it includes analyzing a brain wave generated during a brain activity in real-time so as to control a certain device.

The BCI technology may be used as a medical technology. When it is applied to a patient who lost a part of her/his body or whose body is paralyzed, it can enhance the satisfaction with life.

The BCI technology may use electrodes to learn what the brain wave means. Typically, to perform the BCI, a number of electrodes are installed into the brain of a subject commonly at different positions inside or outside the skull, and the BCI communicates with the subject by observing when and at which frequency a brain wave is detected from at least one of the electrodes.

However, the brain wave exhibits different results even under the same test conditions, depending on the location, time, mental state of the subject, hindrance, and the like. Herein, the metal state may include a thinking of abstract situations, a motor imagery (MI) (e.g., thinking of right hand action and thinking of left hand action), etc. If the test is carried out with another subject, the brain wave may exhibit more different results in the same test.

In order to accurately perform the BCI even though test conditions are changed due to these problems, a variety of filters have been introduced. For instance, "Optimal spatial filtering of single trial EEG during imagined hand movement" by Ramoser H, Muller-Gerking J and Pfurtscheller G, *IEEE Trans. Rehabil. Eng.*, 2000 December; 8(4): 441-6; and "Optimizing Spatial filters for Robust EEG Single-Trial Analysis" by Blankertz B, Tomioka R, Lemm S, Kawanabe M and Muller K-R, *IEEE Signal Process. Mag.* 2008, vol. 25, 41-56 have been introduced. Such technologies have been introduced as a common spatial pattern (CSP) technology, which extracts brain wave features commonly detected from a number of spatially different brain waves, while the subject is thinking the same thing.

However, the above technologies have a problem that it takes long time to learn whenever the common brain wave is extracted due to the performance variations of brain signals over different sessions or subjects. Even trained CSP filters don't work in real-time and frequently yield biased results. In this case, the CSP filters must be retrained by new training data. Accordingly, they cannot be immediately applied to an emergency patient such as a quadriplegia patient and thus the patient must wait for a long time. In addition, the above technologies require a great amount of times for experiments to develop the BCI technology, and accordingly the BCI technology progresses too slowly.

SUMMARY

The present disclosure is proposed in the background as described above, and provides an apparatus and method for a brain computer interface (BCI) having a classifier which instantly distinguishes brain waves even in an emergency.

The present disclosure provides an apparatus and method for a brain computer interface which can accurately detect the state of the brain wave of a subject under various test conditions.

The present disclosure provides an apparatus and method for a brain computer interface to enable a test of the BCI to be quickly executed.

In order to quickly and accurately classify a brain wave, an apparatus for a brain computer interface (BCI) is described including a feature extraction filter trainer for training a feature extraction filter which minimizes an influence of a background brain wave while maximizing a difference between intended brain waves; and a classifier trainer for training the intended brain wave by using a feature vector obtained by filtering the intended brain wave at the feature extraction filter.

The apparatus may include an electroencephalograph for measuring the background brain wave and the intended brain wave; a preprocessor for preprocessing the background brain wave and the intended brain wave; and a brain wave classifier for classifying, through the classifier, any intended brain wave measured by the electroencephalograph. Therefore, the operation of the interface is instantly performed through the brain wave in a clinic. The feature extraction filter filters at least one of spatial information, frequency information, and temporal information to separate a variety of thoughts through the brain wave.

According to the apparatus, when the feature extraction filter filters spatial information, the feature extraction filter may be acquired as $$\max_{w_{[i]}} \left( \frac{w_{[i]}^T C_{[i]} w_{[i]}}{w_{[i]}^T C_{[i]^c} w_{[i]}} \right) \text{ and } \min_{w_{[j]}} (w_i^T \Xi \, w_j),$$

where i is a label, $w_i$ is the feature extraction filter, C is a covariance of the intended brain wave, and $\Xi$ is a covariance of the background brain wave. According to the modeling, the brain wave may be mathematically accurately modeled. Herein, the feature extraction filter is modeled as $$\max_{w_{[i]}} \left( \frac{w_{[i]}^T C_{[i]} w_{[i]}}{(1-\xi) w_{[i]}^T C_{[i]^c} w_{[i]} + \xi P(w_{[i]})} \right) \text{ with } P(w) = w^T \Xi \, w,$$

wherein $\xi$ a certain parameter value. According to this, an optimal solution can be found by the computer calculation.

According to the apparatus, when the feature extraction filter filters spatio-temporal information, the feature extraction filter may be acquired as $$\max_{\gamma_{[1,2]}} \left( \frac{\Gamma_{\{i\}}^T \hat{C}_{\{i\}} \Gamma_{\{i\}}}{(1-\xi)\Gamma_{\{i\}}^T \hat{C}_{\{i\}^c} \Gamma_{\{i\}} + \xi P(\Gamma_{\{i\}})} \right) \text{ with } P(\Gamma) = \Gamma^T \hat{\Xi} \Gamma \text{ and } i \in \{1, 2\}.$$

Herein, i is a label, $\Gamma_{\{i\}}$ a feature extraction filter, is a $\hat{\Xi}$ covariance of the background brain wave, and is a covariance $\hat{C}_{\{i\}}$ of the intended brain wave. According to this, a modeling in which can employ a spatio-temporal filter to more accurately measure the brain wave may be build up.

The apparatus may further include a background brain wave difference value calculation unit for calculating a difference value between a previous background brain wave previously measured and a current background brain wave currently measured; a classifier bias prediction unit for predicting a classifier bias by using the feature extraction filter, the current background brain wave and the classifier; and a classifier calibration unit for calibrating the classifier by using a classifier bias predicting value predicted by the classifier bias prediction unit. According to the apparatus, an accuracy of measuring the brain wave may be further improved.

The background brain wave difference value calculation unit acquires a difference value between the previous background brain wave and the current background brain wave as $$S = \frac{\tilde{D}_{KL}(\Xi_{day1}, \Xi_{day2})}{\max(\tilde{D}_{KL}(\Xi_{day1}, I), \tilde{D}_{KL}(\Xi_{day2}, I))}.$$

Herein, is a covariance $\hat{\Xi}_{day1}$ previous background brain wave, is a covariance $\hat{\Xi}_{day2}$ current background brain wave, I is a unit matrix, and, is a symmetric K-L distance $\tilde{D}_{KL}$ between elements. According to this, the brain wave may be more accurately classified by reflecting a difference between the current background brain wave and the previous background brain wave.

The classifier bias prediction unit may calculate the classifier bias predicting value by substituting a predicted transition value, which is obtained by orthogonally projecting the current background brain wave to the feature extraction filter, predicted from the feature extraction filter, to the classifier. According to this, the value of bias may be more accurately predicted. Herein, the classifier calibration unit may scale the classifier bias predicting value to a difference value between the previous background brain wave and the current background brain wave and transits an offset value of the classifier. According to this, the difference value between the brain waves based on the measuring time point can be corrected to enable the bias to be more accurately predicted.

In order to quickly and accurately classify a brain wave, an method for a brain computer interface (BCI) is described including training a feature extraction filter which minimizes an influence of a background brain wave while maximizing a difference between intended brain waves; and training the intended brain wave by using a feature vector obtained by filtering the intended brain wave at the feature extraction filter.

According to the method, the background brain wave used to train the feature extraction filter and the classifier is newly measured session-by-session to enhance the reliability in the classifying the brain wave. Further, the session newly measures only the background brain wave, and the session the intended brain wave is not newly measured but stored information may be used. According to this, since the intended brain wave needs not to additionally be measured each time and the preceding intended brain wave is reused, thereby quickly the test result, the industrial application can be rapidly achieved and researchers can also rapidly know.

According to the method, the classifier may be calibrated by using the difference value between the previous background brain wave and the current background brain wave. Further, the classifier may be also calibrated by using as a factor a value for correcting an overlapping portion between the feature extraction filter and the current background brain wave. In addition, an offset value may be corrected in the classifier. According to this, there is an effect where the more accurate classification of the brain wave can be achieved.

According to the present disclosure, it is possible to figure out what the brain wave means quickly and accurately by newly measuring the background brain wave only and reusing the preceding brain wave, without measuring the intended brain wave every time. Accordingly, the present disclosure can be applied even in an emergency, and detect what the brain wave means without being affected by various factors inside and outside the subject. Furthermore, experiments relating to the BCI can be carried out more quickly, and thus the BCI technology can progress faster.

BRIEF DESCRIPTION OF DRAWINGS

FIG. 5 is a table illustrating the result of test performance.

DETAILED DESCRIPTION

Hereinafter, specific embodiments of the present disclosure will be described in detail with reference to the accompanying drawings. However, the spirit of the present disclosure is not limited to the specific embodiments provided below, and although the modifications, the equivalents, or the alterations falling into the spirit and the scope of the present disclosure are easily made by those skilled in the art understanding the spirit of the present disclosure, they also fall into the spirit of the present disclosure.

<First Embodiment>

Figure 1:
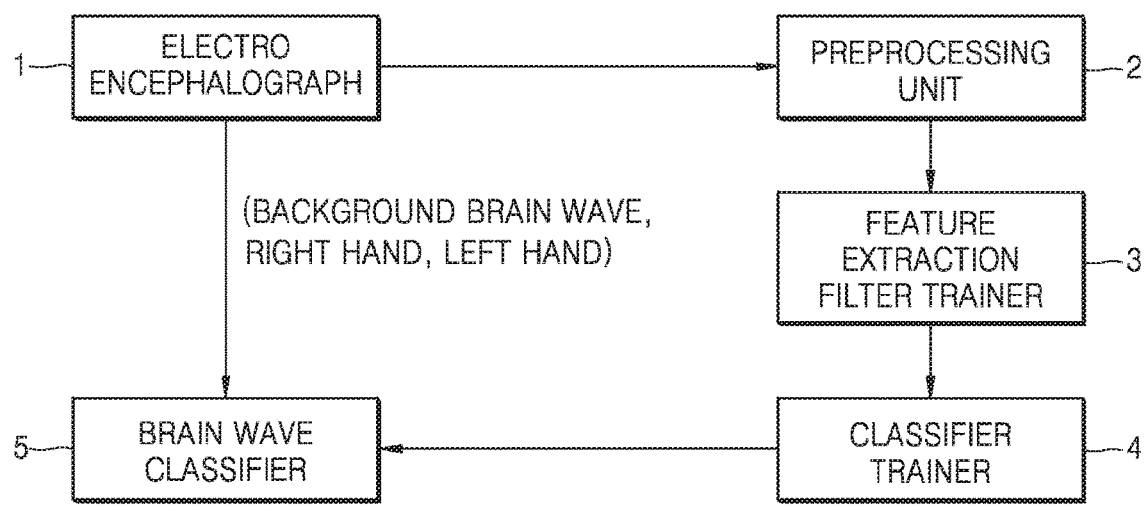
FIG. 1 is a block diagram of an apparatus for a brain computer interface according to a first embodiment of the present disclosure.

FIG. 1 is a block diagram of an apparatus for a brain computer interface according to the first embodiment of the present disclosure.

Referring to FIG. 1, the apparatus for the brain computer interface may include an electroencephalograph 1 installed in a brain for measuring brain waves; a preprocessing unit 2 for performing preprocessing such as extracting a brain wave for a significant portion from the brain waves measured by the electroencephalograph 1; a feature extraction filter trainer 3 for training feature extraction filter which minimize influences from a background brain wave while maximizing a difference between intended brain waves; a classifier trainer 4 for training a classifier by using the feature extraction filter obtained from the feature extraction filter trainer 3; and a brain wave classifier 5 for classifying brain waves obtained by a current test, i.e., intended brain waves by using the classifier obtained from the classifier trainer 4.

A process of obtaining the classifier by using the electroencephalograph 1, the preprocessing unit 2, the trainer 3 and the classifier trainer 4 can obtain a satisfactory result within 30 minutes to an hour. Therefore, the brain wave classifier 5 using the classifier can immediately obtain the result of classifying brain waves for a subject. This means that, when a quadriplegia patient who has cognitive skills but not motor skills visits a hospital, the patient can be subject to the BCI within an hour.

The electroencephalograph 1 may measure a space (which may refer to electrodes installed at various different positions in a brain), a time (which may refer to aspects of a brain wave differently detected over time), and a frequency (which may means different frequencies contained in the brain wave). It is typically known that the electroencephalograph 1 is an apparatus worn outside a skull with a plurality of electrodes installed. It is to be understood that results can be more accurate if the electroencephalograph 1 is installed inside a skull.

The preprocessing unit 2 extracts generally known brain waves from among the entire data measured by the electroencephalograph 1. For example, during a motor imagery (MI) with a subject's right hand and left hand, a brain wave measured by at least one electrode, i.e., signals measured at a frequency band of 8 to 10 Hz or at a time between 0.5 and 2 seconds after beginning the test, may be extracted. It is to be understood that when the subject imagines another situation, signals of other electrodes (spatial), different frequencies, and different times (temporal) may be extracted.

The operations of the feature extraction filter trainer 3 are now described in more detail.

A background brain wave (background noise information) is a type of brain wave which may be extracted when a subject is thinking of nothing. A feature brain wave (feature information) is a type of brain wave which may be extracted when a subject has an intent.

The background brain wave may be extracted even when the feature extraction filter is used, and thus may be mixed with the feature brain wave extracted by the feature extraction filter. An intended brain wave refers to the feature brain wave mixed with noises, and thus is a type of brain wave which may be extracted when a subject has an intent (e.g., moving his/her right hand or left hand). The feature extraction filter trainer 3 may perform a process of minimizing influences of the background brain wave while maximizing a difference between intended brain waves.

The train operations of the feature extraction filter trainer 3 may be performed by using the background brain wave measured when a subject is thinking of nothing and the intended brain wave measured when the subject has an intent. To acquire a sufficient amount of data, the extraction of information on the background brain wave and the intended brain wave may be repeatedly performed dozens of times. At this time, the acquisition of the background brain wave and the intended brain wave may be continuously made by the electroencephalograph 1. The background brain wave may be measured within a short time of about few minutes, and the intended brain wave may be measured within tens of minutes for the acquisition of the exact information.

The feature extraction filter trained by the above process may minimize the influences of the background brain wave while maximizing a difference between intended brain waves. Therefore, the feature brain wave can be detected accurately and the communications with the subject can be carried out more accurately.

The preprocessing unit 2 and the feature extraction filter trainer 3 may selectively use spatial information and temporal information of the brain waves. This is because aspects of the brain wave may vary depending on the intended brain wave. For example, the preprocessing unit 2 and the feature extraction filter trainer 3 may select and use the spatial information obtained from one of the electrodes. Further, the preprocessing unit 2 and the feature extraction filter trainer 3 may use information measured by an electrode at a certain time. In addition, the preprocessing unit 2 and the feature extraction filter trainer 3 may use information at a certain frequency band. That is, the feature extraction filter may be provided as a spatial filter, a temporal filter, or a spatial-temporal filter. In some implementations, it may use time information in which frequency and time are separated. This may be determined depending on thought information which the BCI tries to know, i.e., what the BCI wants from the subject.

The classifier trainer 4 may perform a process of filtering the intended brain wave by the feature extraction filter to generate a feature vector, and training the classifier by the feature vector. The process of training the classifier may employ a Fisher's Linear Discriminant Analysis (FLDA) using a hyperplane, a Support Vector Machine (SVM), or the like.

The brain wave classifier 5 may operate the classifier provided from the feature extraction filter trainer 3 and the classifier trainer 4 to associate the intended brain wave provided from the subject with the thought of the subject.

The brain computer interface may relatively accurately figure out the thought of the subject in about an hour.

Figure 2:
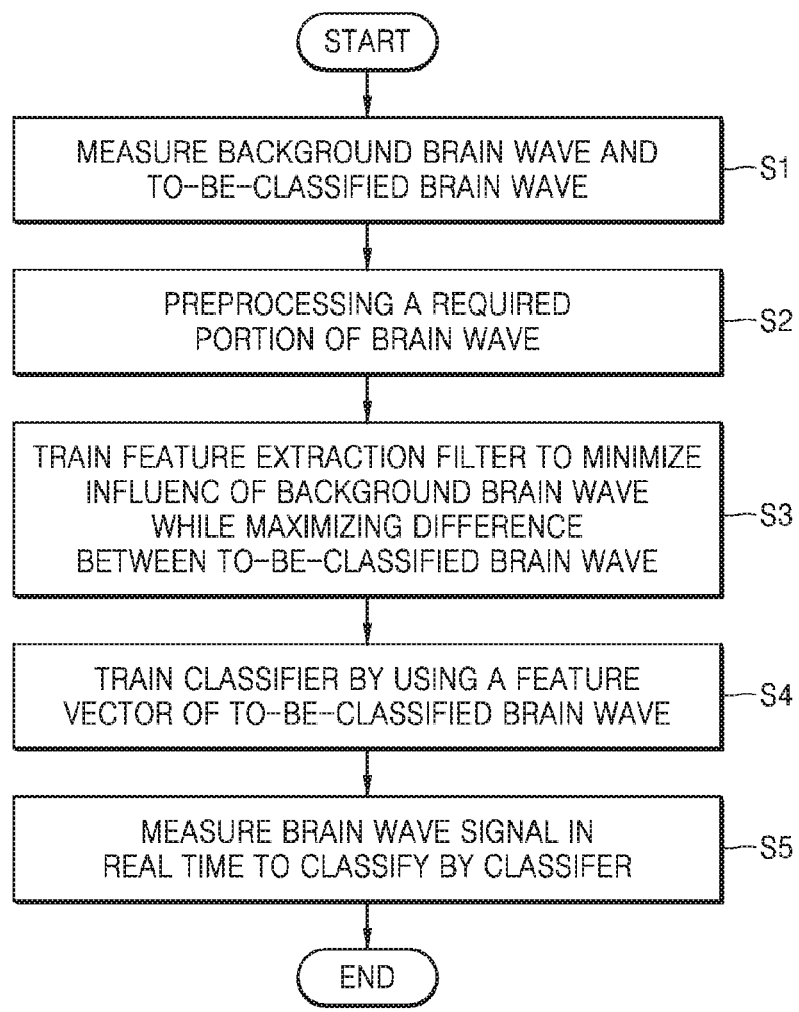
FIG. 2 is a flowchart illustrating a method for the brain computer interface according to the first embodiment of the present disclosure.

FIG. 2 is a flowchart illustrating a method for the brain computer interface according to the first embodiment of the present disclosure. Referring to FIG. 2, a specific embodiment of the apparatus for the brain computer interface as shown in FIG. 1 would be accurately understood as well.

The brain wave of the subject is measured using the electroencephalograph 1. At this time, both of the intended brain wave and the background brain wave may be measured (S1). Temporal and spatial information in the measured brain wave may be roughly preprocessed by the preprocessing unit 2 such that only brain wave information requiring strict analysis can be extracted (S2).

Thereafter, the feature extraction filter capable of extracting the brain wave is trained such that the influences of the background brain wave is minimized, and the differences between to-be-classified brain waves, i.e., the intended brain wave maximized (S3). The intended brain wave contains the feature brain wave and noise, and the feature brain wave may be a brain wave which, when the subject is put on a state of respectively thinking his/her right hand and left hand during the MI as described above by way of illustration, enables the BCI to distinguish which hand the subject is thinking. Hereinafter, the feature brain wave will be described considering that the subject is thinking of moving his/her right hand or left hand by way of illustration.

The process S3 of training the feature extraction filter will be described in more detail.

It has been described above that described above, the feature extraction filter minimizes influences of the background brain wave while maximizing a difference between intended brain waves. This may be represented by Equation 1 as follows:

$$\max_{w_{\{i\}}}\left(\frac{w_{\{i\}}^T C_{\{i\}} w_{\{i\}}}{w_{\{i\}}^T C_{\{i\}^c} w_{\{i\}}}\right) \text{ and } \min_{w_{\{j\}}}(w_i^T \Xi\ w_j) \qquad \text{[Equation 1]}$$

where i is a label denoted by 1 when the subject is thinking his/her right hand and by 2 when the subject is thinking his/her left hand. The symbol $w_i$ is a weighting on the feature extraction filter and is a value which may be varied depending on spaces, i.e., electrodes. A brain wave signal intended to not use is applied 0 or a low weighting while a brain wave intended to use is applied high weighting. C is a covariance of intended brain waves. The subscript c in indication $C_{\{i\}^c}$ complentary set, and thus $\{i\}^c$ indicates a covariance of labels exceptional for i. The symbol $\Xi$ is a covariance of background brain waves.

It would be understood from Equation 1 that the differences between the intended brain waves are maximized (left side term in Equation 1) and common features between the background brain wave and the feature extraction filter are minimized (right side term in Equation 1) when optimizing and training the feature extraction filter.

Minimizing the common features between the background brain wave and the feature extraction filter is such that the feature extraction filter does not extract the background brain wave. In specific, in view of a 2-dimensional plane along which spots of the electrodes are mapped, it may be such that weightings are established to not overlap patterns of the background brain wave and the feature extraction filter.

The Equation 1 is difficult to solve, and hence can be remodeled to Equation 2 as follow:

$$\max_{w_{\{i\}}}\left(\frac{w_{\{i\}}^T C_{\{i\}} w_{\{i\}}}{(1-\xi)w_{\{i\}}^T C_{\{i\}^c} w_{\{i\}} + \xi P(w_{\{i\}})}\right) \text{ with } P(w) = w^T \Xi\ w \qquad \text{[Equation 2]}$$

Equation 2 is remodeled in a manner that the right side term in Equation 1 is transposed to a denominator of the left side term in Equation 1 and a denominator of the right side term in Equation 1 is minimized, thereby maximizing the left side term in FIG. 1.

Various optimizing techniques other than the embodiment above may be employed. In FIG. 2, $\Xi$ may be understood to be a certain parameter value.

Equation 2 is associated with a matter of eigenvectors and equivalently transformed to Equation 3 as a generalized matter of eigenvectors.

$$C_{\{i\}} w_{\{i\}} = \lambda((1-\xi)C_{\{i\}^c} + \xi \hat{\Xi}) w_{\{i\}} \qquad \text{[Equation 3]}$$

Equation 3 may be optimized for a label, i.e., for each of the right hand and left hand. By means of Equation 3, the feature extraction filter may be trained and provided.

Equations 1 to 3 above are applied to only spatial information, i.e., spatial filter for filtering electrodes measuring a brain wave. However, these are not limited thereto and may be also applied to a spatio-temporal filter.

The modeling of Equation 2 applied to use the spatial filter may be replaced with Equation 4 as follows:

$$\max_{\gamma_{\{1,2\}}}\left(\frac{\Gamma_{\{i\}}^T \hat{C}_{\{i\}} \Gamma_{\{i\}}}{(1-\xi)\Gamma_{\{i\}}^T \hat{C}_{\{i\}^c} \Gamma_{\{i\}} + \xi P(\Gamma_{\{i\}})}\right) \text{ with } P(\Gamma) = \qquad \text{[Equation 4]}$$

-continued $$\Gamma^T \hat{\Xi} \Gamma \text{ and } i \in \{1, 2\}$$

where, $\Gamma_{\{i\}}$ is a feature extraction filter utilizing both temporal and spatial information, $\hat{\Xi}$ is a covariance of the background brain wave utilizing both temporal and spatial information, and $\hat{C}_{\{i\}}$ covariance of the intended brain wave utilizing both temporal and spatial information. This case is also to classify the subject's left and right hand, and hence, there are two labels, label 1 and label 2.

Equation 4 is associated with a matter of eigenvectors and equivalently transformed to Equation 5 as a generalized matter of eigenvectors.

$$\hat{C}_{\{i\}} \Gamma_{\{i\}} = \lambda((1-\xi)\hat{C}_{\{i\}^c} + \xi \hat{\Xi}) \Gamma_{\{i\}}, \ i \in \{1,2\} \qquad \text{[Equation 5]}$$

Solving Equation 5 may allow the feature extraction filter utilizing both temporal and spatial information to be trained.

The feature extraction filter provided in the process of training the feature extraction filter (S3) is used to extract the features of the intended brain wave and form feature vectors of the feature brain wave. The features vectors are used to train the classifier (S4). Herein, an algorithm of training the classifier may include FLDA using a hyperplane, SVM, etc.

In the above process, the measurement step (Si) of the brain wave is executed about 30 minutes and the other steps is simply executed. As a result, the classifier may be trained within a time of about 30 minutes to an hour.

Provided the trained classifier, the brain wave of the subject may be measured and communicated in real time from the current time (S5).

According to the first embodiment, the operations of the BCI may be performed utilizing the brain wave of the subject over a time of an hour. Further, a feature extraction filter minimizing the influences of the background brain wave is provided. The feature extraction filter optimized for the subject at the current time point allows the accuracy of the BCI to be enhanced.

<Second Embodiment>

The second embodiment is similar to the first embodiment in many portions, but is such that a more accurate classifier is obtained when the brain waves of the subject can be measured session-by-session. The session means that a new background brain wave is measured in a situation where the background brain wave may be varied. For example, the session may be measured once a day. The specific description of the same portions of the second embodiment as the first embodiment is omitted because the first embodiment has been described already.

FIG. 2 is a block diagram of an apparatus for a brain computer interface according to the second embodiment of the present disclosure.

Figure 3:
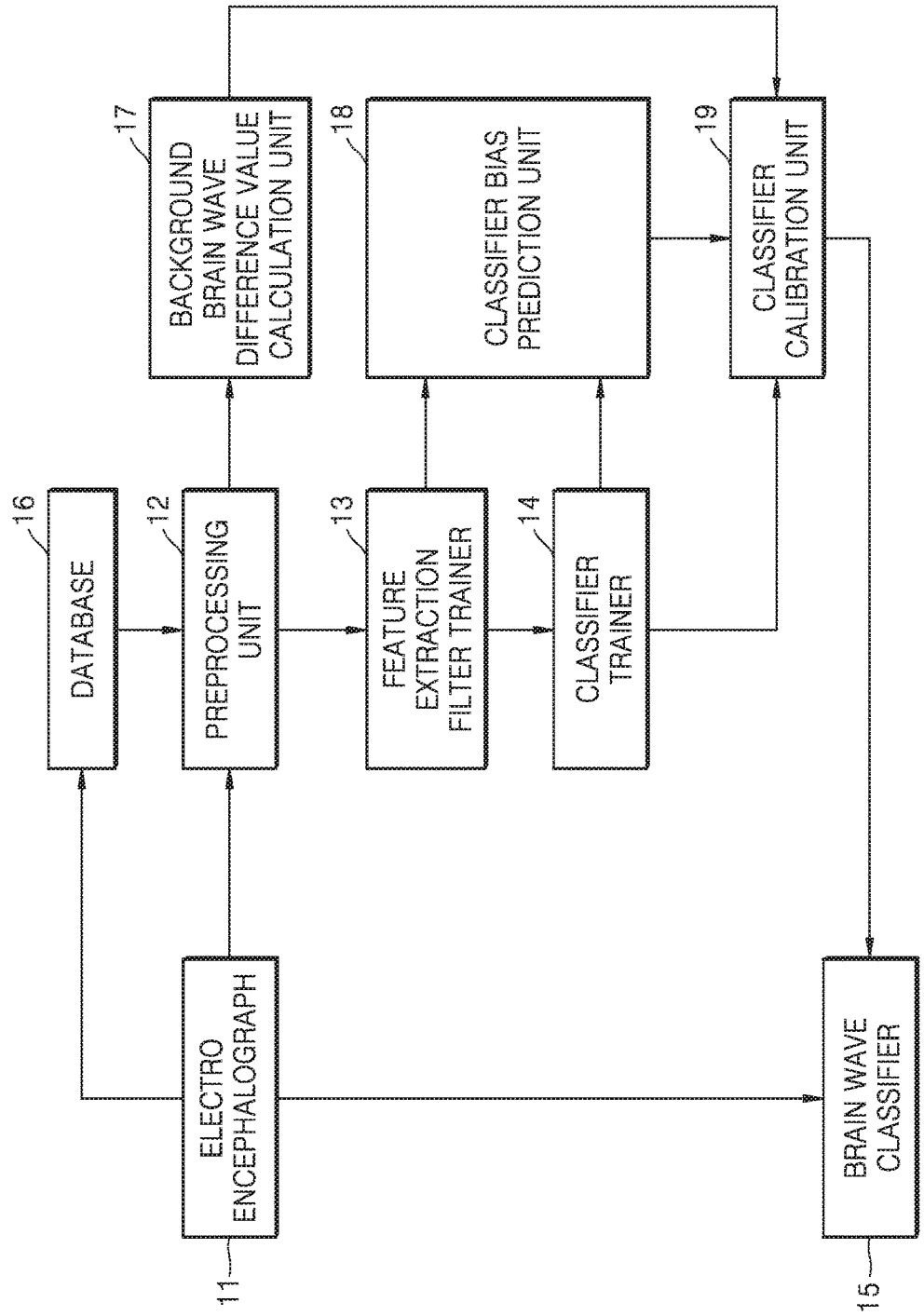
FIG. 3 is a block diagram of an apparatus for a brain computer interface according to a second embodiment of the present disclosure.

Referring to FIG. 3, the apparatus for the brain computer interface may be provided with an electroencephalograph 11, installed in a brain, for measuring brain waves; a preprocessing unit 12 to execute preprocessing such as extracting a brain wave for a significant portion from the brain waves measured by the electroencephalograph 11; a feature extraction filter trainer 13 for training feature extraction filter which minimize influences from a background brain wave while maximizing a difference between intended brain waves; a classifier trainer 14 for training a classifier by using the feature extraction filter; and a brain wave classifier 15, trained by the classifier trainer 14, for classifying a brain wave currently being obtained by a test.

In addition, the apparatus for the brain computer interface may further includes a database 16 for storing thereon brain waves measured by the electroencephalograph 11, a background brain wave difference value calculation unit 17 for calculating a difference value of a current background brain wave relative to two background brain waves measured in different sessions (e.g., a current session and a preceding session) processed by the preprocessing unit 11, a classifier bias prediction unit 18 for predicting a classifier bias by using a feature extraction filter extracted by the feature extraction filter trainer 13 and a classifier extracted by the background brain wave and the classifier trainer 14, and a classifier calibration unit 19 for calibrating the classifier by using the difference value of the background brain waves provided to the background brain wave difference value calculation unit 17 and a classifier bias prediction value provided from the classifier bias prediction unit 18.

According to the apparatus, the classifier may be more accurately calibrated by using the difference value between the current background brain wave and the previous background brain wave, and information which the feature extraction filter and the background brain wave are mixed.

Meanwhile, the database 16 may store the background brain wave and the intended brain wave. The background brain wave and the intended brain wave may be measured and stored every session. The background brain wave may be stored session-by-session, and the intended brain wave may not vary according to sessions but any intended brain wave obtained from any one session may be used in common for sessions. This is because the intended brain wave may be measured from any one session many times to obtain an exact value without variations.

Figure 4:
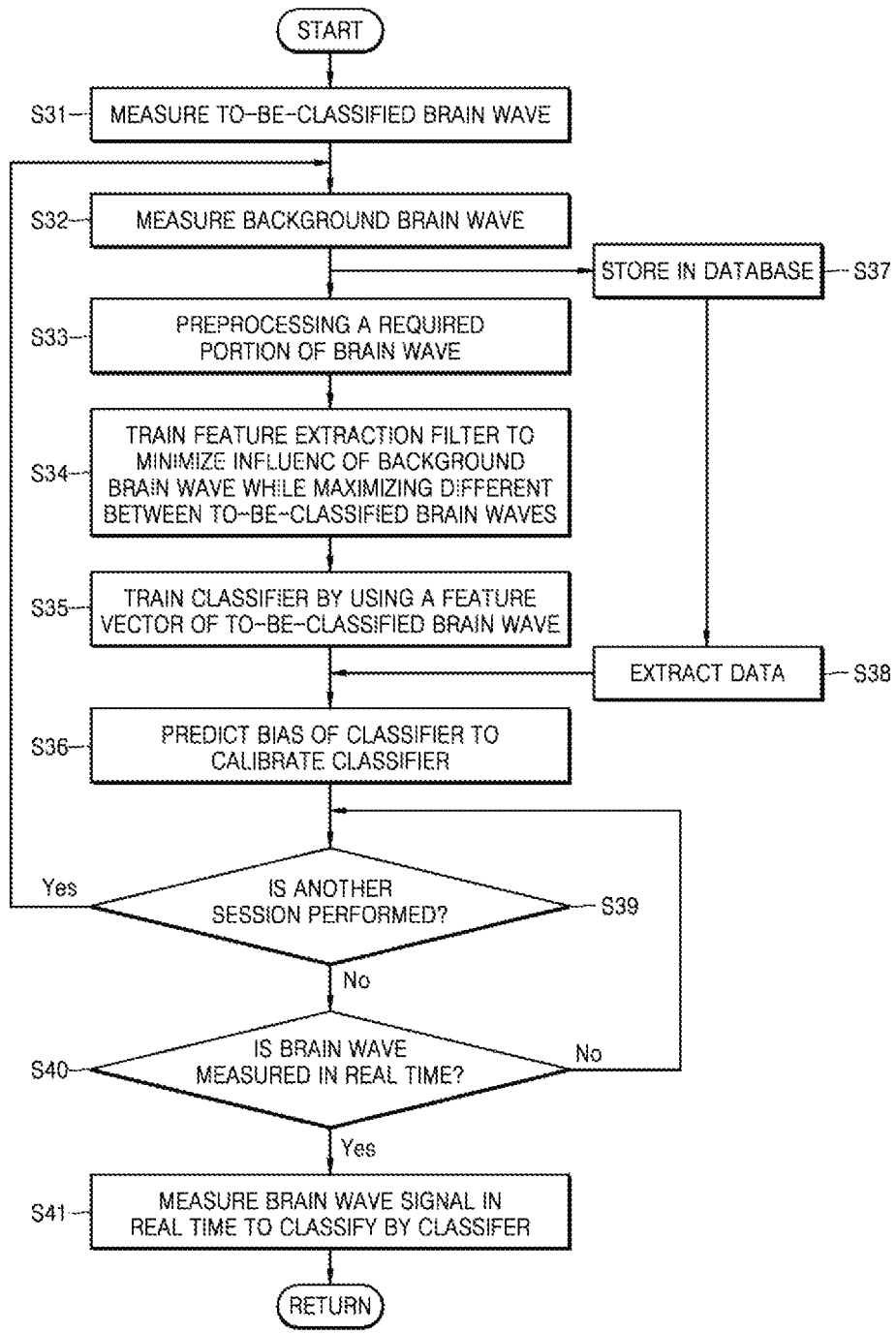
FIG. 4 is a flowchart illustrating a method for the brain computer interface according to the second embodiment of the present disclosure.

FIG. 4 is a flowchart illustrating a method for the brain computer interface according to the second embodiment of the present disclosure. Referring to FIG. 4, a specific embodiment of the apparatus for the brain computer interface as shown in FIG. 3 would be accurately understood as well.

Referring to FIG. 4, the intended brain wave which becomes the to-be-classified object is measured (S31). Thereafter, the background brain wave is measured (S32). The background brain wave and the intended brain wave, which are measured in a current time point are stored in the database (S37). As the session is repeated, the background brain wave and the intended brain wave are accumulated and stored in the database 16. The intended brain wave may be not a single one, and may be measured session-by-session when the subject has time on his/her side and stored along with its classified results in the database. Merely, the background brain wave is necessarily executed every session and is stored in the database.

The previous background brain wave, whose feature brain waves are accurately classified, of the brain waves stored in the database and the current background brain wave are preprocessed (S33).

Thereafter, the influences of the current background brain wave are minimized, and the feature extraction filter is trained such that a difference between the intended brain waves to be classified is maximized (herein, the intended brain waves may be intended brain waves obtained from the session executed while the previous background brain waves are measured) (S34). Then, the intended brain wave is filtered using the feature extraction filter to extract of feature vectors of the feature brain wave, thereby training the classifier (S35). In such a manner, the classifier may be calibrated more accurately whether the intended brain wave is measured or not. Of course, the first repetition step may use the current to-be-classified brain wave as the intended brain wave since there is no to-be-classified brain wave.

Although the preprocessing process (S33), the feature extraction filter training process (S34), and the classifier training process (S35) may be meager, the meager description is applied the description of the first embodiment.

After the classifier is obtained, in order to improve the difference between the respective background brain waves session-by-session and incompleteness of the feature extraction filter, a classifier bias is predicted and used to calibrate the classifier (S36).

The process S36 of calibrating the classifier will be described in more detail.

First of all, correction of the difference value of the background brain waves will be described. To do so, the difference value, which may be a value extracted from the database (S38), between the current background brain wave and the previous background brain wave is a normalized value.

For example, in a certain data group, a Kullback-Leibler distance (K-L distance) is used to calculate a distance between two data distributions. In specific, Equation 6 having a numerator of a K-L distance between the two background brain waves and a denominator of a K-L distance between the respective two background brain waves and a unit matrix is defined as follows:

$$S = \frac{\tilde{D}_{KL}(\tilde{\Xi}_{day1}, \tilde{\Xi}_{day2})}{\max(\tilde{D}_{KL}(\tilde{\Xi}_{day1}, I), \tilde{D}_{KL}(\tilde{\Xi}_{day2}, I))} \quad \text{[Equation 6]}$$

wherein, $\hat{\Xi}_{day}1$ is a covariance of the previous background brain wave, $\hat{\Xi}_{day2}$ is a covariance of the current background brain wave, I is a unit matrix, and, $\tilde{D}_{KL}$ indicates a symmetric K-L distance between elements.

According to Equation 6, the difference value between the current background brain wave and the previous background brain wave may be found as the normalized value. Also, to find the difference value between the current background brain wave and the previous background brain wave, other methods not using such a K-L distance may be employed. The difference value between the current background brain wave and the previous background brain wave may be subsequently used as a value for scaling the bias prediction value of the classifier.

The correction of the incompleteness, i.e., biasing, of the feature extraction filter will be explained. The current background brain wave is orthogonally projected to the feature extraction filter obtained in the process of S34 to find predicted transition values predicted from the respective feature extraction filters. The predicted transition values may be given by Equation 7:

$$\phi_i = \log(w_i^T \hat{\Xi} w_i) \quad \text{[Equation 7]}$$

Equation 7 may indicate a value which, because information extracted through the feature extraction filter ($w_i$) may overlap that of the current background brain wave, can correct such an overlapped portion. If there is no overlapped portion, Equation 7 would result in zero. Taking a log value may be additionally performed because a log scale is used in the training process of the classifier S35.

The predicted transition values may be provided for the respective feature extraction filters so that they may be collected and represented by a vector, and the classifier bias prediction value may be finally represented by Equation as follows:

$$\varepsilon = w_{FLDA}^T \Phi + w_{FLDA\_offset} \quad \text{[Equation 8]}$$

wherein ε is a classifier bias prediction value, $w_{FLDA}^T$ is a slope value of the classifier obtained by the FLDA method, which may be merely an example, in the process of training the classifier S35, and $w_{FLDA\_offset}$ be a value of a nodal point where the classifier obtained by the FLDA method in the training process of the classifier (S35) passes through a reference axis. The bias prediction value of the classifier can be calculated by the method above. Equation 8 is also merely an example.

Finally, the bias prediction value ε of the classifier is scaled to a difference value S between the current background brain wave and the previous background brain wave and then the classifier is calibrated. Scaling the bias prediction value ε of the classifier to the difference value S between the current background brain wave and the previous background brain wave is because the bias prediction value ε of the classifier is predicted using the current background brain wave (see Equation 7) and intended brain wave is a brain wave when the previous background brain wave is measured. The intended brain wave is not significantly varied and it takes much time to measure the intended brain wave session-by-session. Therefore, in order to accommodate for the convenience of the subject, the classifier is calibrated as described above.

Equation 9 represents the calibration of the classifier.

$$\{w_{FLDA}, w_{FLDA\_offset} - S\varepsilon\} \quad \text{[Equation 9]}$$

As seen from Equation 9, the value of the nodal point (which may be referred to as an offset value) of the classifier with the axis is shifted by Sε.

The calibration process of the classifier (S36) may be continuously performed session-by-session (S39). The calibration of the classifier continuously performed session-by-session may increase the accuracy of the classifier. Therefore, the classifier which can accurately operate any time may be obtained when the background brain wave of the subject is measured.

Unless the classifier is improved in other session, it is determined whether a to-be-classified brain wave is newly measured (S40), and the to-be-classified brain wave is measured and classified using the classifier calibrated in the classifier calibration process S36 of the classifier (S41).

FIG. 5 is a table illustrating the result of test performance.

FIG. 5 shows the comparison of the session-by-session test results for a scheme of using a common spatial pattern (CSP) (first column), a scheme of using an invariant common spatial pattern (iCSP) introduced in "Invariant common spatial patterns: alleviating nonstationarities in brain computer interfacing" by Blankertz B, Kawanabe M, Tomioka R, Hohlefeld F U, Nikulin V and Muller K-R, 2008, *Adv. Neural Inform. Process. Syst.* 20 113-2 (second column), a scheme of using an embodiment of the present disclosure for minimizing the background brain wave and using the iCSP at the same time (third column), a scheme of using a stationary common spatial pattern (sCSP) introduced in "Stationary common spatial patterns for brain computer interfacing" by Samek W, Vidaurre C, Muller K-R and Kawanabe M, 2012, *J. Neural Eng.* 9 026013 (fourth column), a scheme of using a regularized spatiotemporal filter (RSTF) (fifth column), a scheme of using an embodiment of the present disclosure for minimizing the background brain wave (first embodiment) and using the RSTF at the same time (sixth column), and a scheme of using an embodiment of the present disclosure for minimizing the background brain wave (first embodiment) and an embodiment of the present disclosure for calibrating the classifier (second embodiment) and using the RSTF at the same time (a seventh column).

As can be seen from the test, the classifier to which the scheme of minimizing the background brain wave and/or the scheme of calibrating the bias of the classifier is applied can most successfully serve as the BCI.

The embodiment of the present disclosure may further include another embodiment. For example, the bias prediction value of the classifier would be also able to be provided by another arithmetic expression. Further, the better intended brain wave may be acquired by obtaining and storing the intended brain wave at multiple times, thereby obtaining the better classifier.

According to the present disclosure, by using only the background brain wave, increasing the recyclability, an apparatus and method for the BCI may be achieved performing quick operations. Moreover, the spirit of the present disclosure to academic circles as well as industrial circles may be applied to more quickly perform any test, and therefore, the application thereof may be highly anticipated.

What is claimed is:

1. An apparatus for a brain computer interface (BCI), comprising:
    an electroencephalograph configured to measure brain waves including a background brain wave and intended brain waves; and
    a processor configured to:
    train a feature extraction filter which minimizes an influence of the background brain wave while maximizing a difference between intended brain waves,
    train a classifier for classifying the intended brain waves by using a feature vector obtained by filtering the intended brain waves with the feature extraction filter,
    calculate a classifier bias by using the feature extraction filter, a current background brain wave and the classifier, and
    calibrate the classifier by using the calculated classifier bias,
    wherein the processor calculates the classifier bias by providing a predicted transition value, which is obtained by orthogonally projecting the current background brain wave to the feature extraction filter, predicted from the feature extraction filter, to the classifier.

2. The apparatus according to claim 1, wherein the processor is further configured to:
    preprocess the background brain wave and the intended brain waves, and
    classify, through the classifier, a certain intended brain wave measured by the electroencephalograph.

3. The apparatus according to claim 1, wherein the feature extraction filter filters at least one of spatial information, frequency information, and temporal information of the measured brain waves.

4. The apparatus according to claim 1, wherein the feature extraction filter filters spatial information, and the feature extraction filter is acquired as follows:

$$\max_{w_{[i]}} \left( \frac{w_{[i]}^T C_{[i]} w_{[i]}}{w_{[i]}^T C_{[i]^c} w_{[i]}} \right) \text{ and } \min_{w_{[j]}} (w_i^T \equiv w_j),$$

where i denotes a label, $w_i$ denotes the feature extraction filter, C denotes a covariance of the intended brain wave, and $\Xi$ denotes a covariance of the background brain wave.

5. The apparatus according to claim 4, wherein the feature extraction filter is modeled as follows:

$$\max_{w_{\{i\}}} \left( \frac{w_{\{i\}}^T C_{\{i\}} w_{\{i\}}}{(1-\xi) w_{\{i\}}^T C_{\{i\}^c} w_{\{i\}} + \xi P(w_{\{i\}})} \right) \text{ with } P(w) = w^T \Xi w,$$

where $\xi$ denotes a predetermined parameter value.

6. The apparatus according to claim 1, wherein the feature extraction filter filters spatiotemporal information, and the feature extraction filter is acquired as follows:

$$\max_{\gamma_{\{1,2\}}} \left( \frac{\Gamma_{\{i\}}^T \hat{C}_{\{i\}} \Gamma_{\{i\}}}{(1-\xi) \Gamma_{\{i\}}^T \hat{C}_{\{i\}^c} \Gamma_{\{i\}} + \xi P(\Gamma_{\{i\}})} \right) \text{ with } P(\Gamma) = \Gamma^T \hat{\Xi} \Gamma \text{ and } i \in \{1, 2\},$$

where i denotes a label, $\Gamma_{\{i\}}$ denotes the feature extraction filter, $\hat{\Xi}$ denotes a covariance of the background brain wave, and $\hat{C}_{\{i\}}$ denotes a covariance of the intended brain wave.

7. The apparatus according to claim 1, wherein the processor acquires a difference value between a previous background brain wave and the current background brain wave as follows:

$$S = \frac{\tilde{D}_{KL}(\Xi_{day1}, \Xi_{day2})}{\max(\tilde{D}_{KL}(\Xi_{day1}, I), \tilde{D}_{KL}(\Xi_{day2}, I))},$$

where $\Xi_{day1}$ denotes a covariance of the previous background brain wave, $\Xi_{day2}$ denotes a covariance of the current background brain wave, I denotes a unit matrix, and $\tilde{D}_{KL}$ denotes a symmetric K-L distance between elements.

8. The apparatus according to claim 1, wherein the processor is thither configured to:
calculate a difference value between a previous background brain wave previously measured and a current background brain wave currently measured,
scale the calculated classifier bias to the difference value between the previous background brain wave and the current background brain wave, and
modify an offset value of the classifier based on the scaled calculated classifier bias.

* * * * *